US008000790B2

(12) United States Patent
Björling et al.

(10) Patent No.: US 8,000,790 B2
(45) Date of Patent: Aug. 16, 2011

(54) DEVICE FOR ADJUSTING THE SENSITIVITY LEVEL OF AN IMPLANTABLE MEDICAL DEVICE

(75) Inventors: Anders Björling, Järfälla (SE); Nils Holmström, Järfälla (SE); Karin Järverud, Solna (SE); Martin Obel, Danderyd (SE)

(73) Assignee: St. Jude Medical AB, Jarfalla (SE)

( * ) Notice: Subject to any disclaimer, the term of this patent is extended or adjusted under 35 U.S.C. 154(b) by 101 days.

(21) Appl. No.: 10/576,178

(22) PCT Filed: Oct. 27, 2003

(86) PCT No.: PCT/SE03/01661
§ 371 (c)(1),
(2), (4) Date: Apr. 19, 2006

(87) PCT Pub. No.: WO2005/042090
PCT Pub. Date: May 12, 2005

(65) Prior Publication Data
US 2007/0078488 A1    Apr. 5, 2007

(51) Int. Cl.
*A61N 1/00* (2006.01)
*A61B 5/04* (2006.01)
(52) U.S. Cl. .................. 607/28; 607/2; 607/17; 600/517
(58) Field of Classification Search .................... 607/17, 607/28; 600/517
See application file for complete search history.

(56) References Cited

U.S. PATENT DOCUMENTS

| | | | | |
|---|---|---|---|---|
| 3,757,790 A | * | 9/1973 | Herrmann | 607/28 |
| 3,769,986 A | * | 11/1973 | Herrmann | 607/27 |
| 4,273,132 A | * | 6/1981 | Hartlaub et al. | 607/28 |
| 4,759,367 A | * | 7/1988 | Callaghan | 607/26 |
| 4,858,610 A | * | 8/1989 | Callaghan et al. | 607/13 |
| 4,878,497 A | * | 11/1989 | Callaghan et al. | 607/28 |
| 4,895,152 A | * | 1/1990 | Callaghan et al. | 607/13 |
| 5,184,616 A | * | 2/1993 | Weiss | 607/4 |
| 5,350,410 A | * | 9/1994 | Kleks et al. | 607/28 |
| 5,476,485 A | * | 12/1995 | Weinberg et al. | 607/28 |
| 5,658,317 A | | 8/1997 | Haefner et al. | |
| 5,735,882 A | * | 4/1998 | Rottenberg et al. | 607/27 |
| 6,112,119 A | * | 8/2000 | Schuelke et al. | 607/9 |
| 6,263,244 B1 | * | 7/2001 | Mann et al. | 607/28 |
| 6,408,210 B1 | * | 6/2002 | Bornzin et al. | 607/28 |
| 6,418,343 B1 | | 7/2002 | Zhang et al. | |
| 6,456,882 B1 | * | 9/2002 | Schloss | 607/28 |
| 6,539,259 B1 | * | 3/2003 | Weinberg et al. | 607/9 |
| 6,625,490 B1 | * | 9/2003 | McClure et al. | 607/9 |

(Continued)

FOREIGN PATENT DOCUMENTS

EP    0 958 843    11/1999

(Continued)

*Primary Examiner* — Niketa Patel
*Assistant Examiner* — Nicole F Lavert
(74) *Attorney, Agent, or Firm* — Schiff Hardin LLP (57) ABSTRACT

An implantable cardiac stimulation device has an atrial detector that detects atrial events of a patient's heart, and a memory in which sequences of IEGM signals are stored, having a predetermined length, and an analyzing unit that analyzes the sequences to determine if the stored sequences contain atrial events having a lower amplitude than the current sensitivity setting of the atrial detector. A control unit is connected to the atrial detector to adjust the sensitivity setting thereof to a threshold that is determined based on the aforementioned analysis of the IEGM signals.

4 Claims, 4 Drawing Sheets

U.S. PATENT DOCUMENTS

| | | | |
|---|---|---|---|
| 6,745,074 B1 * | 6/2004 | Obel ................................ | 607/9 |
| 6,748,261 B1 * | 6/2004 | Kroll et al. .................... | 600/510 |
| 2002/0165587 A1 * | 11/2002 | Zhang et al. .................... | 607/28 |
| 2003/0199934 A1 * | 10/2003 | Struble et al. .................... | 607/17 |

FOREIGN PATENT DOCUMENTS

| | | | |
|---|---|---|---|
| EP | 1 072 284 | | 1/2001 |
| EP | 1116495 A2 | * | 7/2001 |
| EP | 1240918 A2 | * | 9/2002 |
| EP | 1264614 A2 | * | 12/2002 |
| EP | 1486231 A | * | 12/2004 |
| WO | WO00/69518 | * | 11/2000 |
| WO | WO0069518 | * | 11/2000 |
| WO | WO 0069518 | * | 11/2000 |
| WO | WO 01/24877 | | 4/2001 |

* cited by examiner

DEVICE FOR ADJUSTING THE SENSITIVITY LEVEL OF AN IMPLANTABLE MEDICAL DEVICE

BACKGROUND OF THE INVENTION

1. Field of the Invention

The present invention generally relates to implantable medical devices such as implantable cardiac pacemakers and in particular to devices for automatically adjusting a sensing threshold of such medical devices.

2. Description of the Prior Art

Modern implantable stimulation devices generally include sensing capabilities, in one or two chambers of the heart. Typically, sensing of the low amplitude cardiac signals is achieved by means of sense amplifier circuits which amplifies and filters electrogram signals obtained by electrodes placed in or on the heart and which are connected by suitable leads to the implantable device. In general, the signals from the sense amplifier are applied to one input of a comparator circuit whose other input is connected to a reference source, i.e. a reference potential. Only in those cases where an electrogram signal from the sense amplifier exceeds the reference potential it will be treated as a detected cardiac depolarization event such as a P-wave (atrial intrinsic depolarization event). The reference potential may thus be referred to as a sensing threshold.

Sensing circuits of the above-mentioned type often fail to sense cardiac depolarizations since the cardiac depolarization events can result in widely different peak amplitudes, depending on e.g. patient activity, body position, and/or drugs being used, etc. Movements of the leads and noise may further restrain the detection of cardiac depolarization events. Noise sources may include environmental noise, such as 50 or 60 Hz power line noise, motion artifacts, or T-waves.

Programmable implantable devices offer a higher degree of flexibility since the physician can change the threshold potential of the comparator but, in spite of this, sensing errors will still occur due to above-mentioned reasons frequently enough to result in, for example, patient discomfort. When the threshold is set too low, the likelihood of over-sensing increases significantly, i.e. erroneous sensing of noise or undesired cardiac signals may occur. On the other hand, if the sensing threshold is set too high the likelihood of under-sensing is increased, i.e. some cardiac event will not be detected.

Furthermore, under-sensing may also cause an R-wave preceded by an atrial event, which may be, for example, a P-wave or a PAC (premature atrial contraction), to be interpreted as a PVC (premature ventricular contraction) due to the fact that the atrial event was not detected by the atrial detecting means. This phenomenon is hereinafter referred to as a false PVC. In particular, with respect to PAC's, the amplitudes of PAC's generally are significantly lower than the amplitudes of sinus induced P-waves, which entails that a PAC is almost impossible to detect using the prior art methods and apparatus for adjusting the sensing thresholds. In certain therapeutical applications it is desirable to identify PVCs, i.e. to identify the source of a PVC in order to distinguish between true PVCs and false PVCs, where a true PVC is an R-wave, without a preceding atrial event. This identification is very useful for diagnostic purposes.

Several attempts have been disclosed addressing the problems associated with under- and/or over-sensing, for example, U.S. Pat. No. 6,418,343, to Zhang et al. entitled "Method an apparatus for adjusting the sensing threshold of a cardiac rhythm management device". The method according to U.S. Pat. No. 6,418,343 is, however, complicated and requires rather extensive calculation capabilities of the controller of the device.

Hence, there is a need for an implantable stimulation device in which the sensing thresholds in an effective and reliable way can be automatically adjusted on a continuous basis by the device itself.

SUMMARY OF THE INVENTION

An object of the present invention is to provide an implantable stimulation device in which the sensing thresholds in an effective and reliable way may be automatically adjusted on a continuous basis by the device itself.

For clarity, the term "true premature ventricular contraction (PVC)" as used herein refers to a detected ventricular event, i.e. R-wave, without a preceding atrial event, such as a P-wave or a premature atrial contraction (PAC). The term "false PVC" as used herein refers to a detected ventricular event without detected preceding atrial event where it is revealed that the ventricular event in fact was preceded by an atrial event not detected for some reason. This may be caused by, for example, a P-wave threshold that is too high, leading to P-waves of lower amplitudes not being detected, such as conducted premature atrial contractions.

The above object is achieved according to the present invention, by an implantable cardiac stimulation device having an atrial detector having an amplifier, the atrial detector having adjustable sensitivity settings, a control unit, and a memory for storing sequences of IEGM signals having a predetermined length. The stimulation device further has a threshold determining unit to determine thresholds for the sensitivity setting based upon identified atrial events, and an analyzing unit to identify atrial events in the stored IEGM signal. The analyzing unit identifies if the stored sequence contains atrial events having a lower amplitude than the current sensitivity setting. The control unit adjusts the sensitivity setting using the identified atrial events in the sequence in the threshold determining unit to assure that the atrial detector detects all atrial events.

Thus, the invention is based on the use of information regarding atrial events in a stored IEGM sequence to automatically adjust the sensing threshold of the atrial detector in order to adapt the current sensing threshold to variations in peak amplitudes of atrial events, for example, P-waves, depending on e.g. patient activity, body position, and/or drugs being used, etc. The current sensing threshold of the sensitivity settings may be the initial sensing threshold, which is based on an atrial event detected by the atrial detector, or a sensing threshold adjusted in accordance with the invention. Accordingly, it is possible to adjust the sensitivity settings in order to allow the atrial detector to detect all atrial events, P-waves as well as PAC's despite the fact that PACs have a significantly lower amplitude that sinus induced P-waves. In this manner, the adjustment of the sensing threshold or thresholds can be very accurately performed and the problems associated with under-sensing and over-sensing can be avoided.

Moreover, a sequence of IEGM signals can be analyzed to obtain statistical information regarding the relation between PACs and P-waves, which can be very useful for, for example, diagnostic purposes.

In a preferred embodiment, the control unit, upon the detection of a predefined cardiac event, adjusts the current sensing threshold of the sensitivity settings by analyzing a sequence of atrial IEGM signals immediately preceding the predefined cardiac event. It is thereby possible to select a cardiac event that will trigger the adjustment procedure or mode of the device. In other words, by utilizing the detection of the occurrence of a predefined cardiac event as an indicator of that the sensitivity settings of the atrial detecting means may have been erroneously determined or set, the stimulation device can be adapted to operate in an effective way in patients suffering from different cardiac disorders since the sensitivity settings of the stimulation device can be automatically adjusted in order to allow the atrial detecting means to detect all atrial events, P-waves as well as PAC's despite the fact that PACs have a significantly lower amplitude than P-waves. Thus, the adjustment of the sensing threshold or thresholds can be more accurately performed since the adjustment mode can be initiated by a pre-selected cardiac event. Furthermore, the pre-selected event can be changed thereby offering high degree of flexibility.

In another embodiment of the present invention, the implantable cardiac stimulation device further has a ventricular detector including an amplifier coupled to the control unit and the control unit, upon the detection of a Premature Ventricular contraction (PVC), determines whether the PVC was a true PVC or an R-wave preceded by a non-detected P-wave by analyzing a sequence of atrial IEGM signals immediately preceding the predefined cardiac event. Thereby, the cause of a PVC can be determined, i.e. whether the event was a true or false PVC, which is highly desirable for therapeutic and diagnostic reasons.

However, there are a number of other conceivable cardiac events or states that may be used to initiate the adjustment mode. As an example, an atrial stimulation and/or a ventricular stimulation can be used for initiating the controlling unit to retrieve a sequence or a number of sequences of stored IEGM signals in order to adjust the current sensing threshold of the sensitivity settings by analyzing the sequence(s).

In another preferred embodiment, the control unit adjusts the atrial sensitivity setting if the detected PVC was caused by a non-detected P-wave. Thereby, the sensitivity setting can be more accurate set and it is also possible to adapt the device to distinguish between true PVCs and R-waves caused by a non-detected P-wave and thereby interpreted as a PVC.

Furthermore, the highest sensitivity setting allowable for the control unit is determined by the actual noise level of the components that obtain and store the sequences of IEGM signals.

According to a preferred embodiment of the invention, the initial sensitivity setting is determined by the measured P-wave amplitude multiplied by a factor in the range 0.4-0.9.

DESCRIPTION OF THE PREFERRED EMBODIMENTS

The present invention provides an implantable stimulation device for automatically adjusting the sensing thresholds of a cardiac rhythm device capable of sensing intrinsic events of a patient's heart. Such devices in which the invention may find application include implantable cardiac pacemakers, cardioverters and defibrillators.

Figure 1:
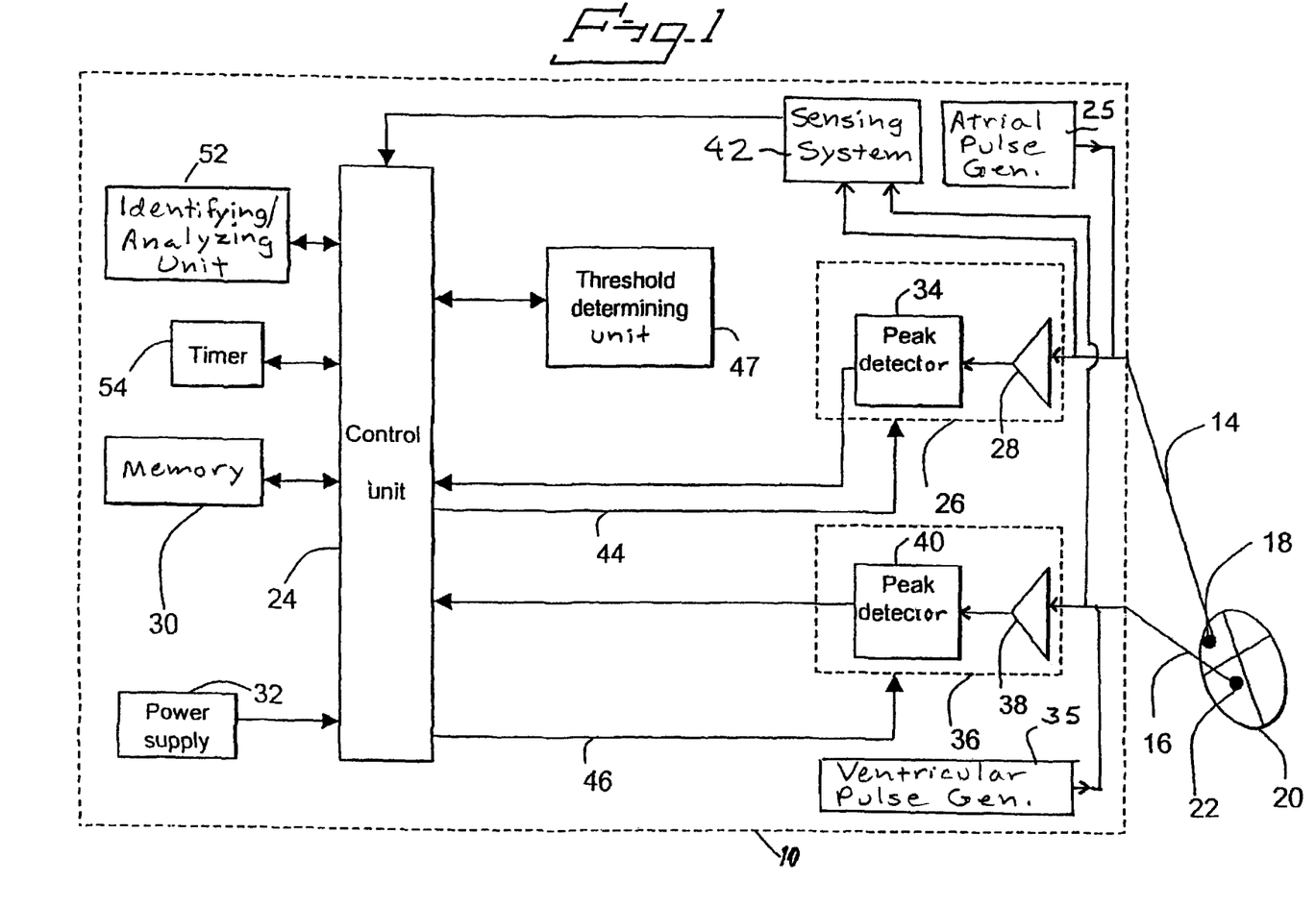
FIG. 1 is a basic block diagram of an implantable cardiac stimulation device that incorporates the automatic adjustment feature according to the present invention.

Referring first to FIG. 1, there is illustrated by means of a block diagram, a hardware platform according to a preferred embodiment of a dual chamber implantable stimulation device 10 according to the present invention capable of automatic sensitivity adjustments in response of atrial and ventricular events.

As shown in FIG. 1, an implantable stimulation device 10 is coupled to a patient's heart 20 by leads 14 and 16 located in the atrium and the ventricle, respectively. The leads 14 and 16 are shown as bipolar single pass VDD or DDD leads, various forms of which are known to those skilled in the art. The atrial lead 14 includes atrial electrode arrangement 18, e.g. an atrial tip electrode and an atrial ring electrode. The ventricular lead 16 includes ventricular electrode arrangement 22, e.g. a ventricular tip electrode and a ventricular ring electrode. In this embodiment, the atrial electrode 18 is placed to detect atrial depolarization, while the ventricular electrode 22 detects ventricular depolarization. Accordingly, the arrangement shown in FIG. 1 can be used for sensing both intrinsic P-waves and ventricular events, such as a PVC (premature ventricular contraction).

A control unit 24 is coupled to a power supply 32 and to a memory 30, which may be a RAM memory, by a suitable data/address bus (not shown). As is well known in the art, the control unit 24 could be constructed from dedicated logic and timing circuitry, state machine circuitry, or a microprocessor. Moreover, the control unit 24 may in any of several forms including a dedicated state device or a microprocessor with code, and may include ROM memory for storing programs to be executed by the control unit 24. Furthermore, the memory 30 can also be included in the control unit 24. The memory 30 allows certain control parameters, used by the control unit 24 in controlling the operation of the implantable device, to be programmably stored and modified, as required in order to customize the operation of the device to suit the needs of a particular patient. Further, data sensed during the operation may be stored in the memory 30 for later retrieval and analysis. For example, sequences of intracardiac electrograms (IEGM's) obtained by a sensing system can be stored in the memory 30, which will be discussed in more detail below.

A telemetry circuit (not shown) is further included in the stimulation device 10. This telemetry circuit is connected to the control unit 24 by means of suitable command/data bus (not shown). In turn, the telemetry circuit may be selectively connected to an external programming device by means of an appropriate communication link, which may be a suitable electromagnetic link, such as an RF link.

For generating stimulation pulses to the appropriate chamber of the heart 20, the control unit 24 further controls an atrial pulse generator 25 and a ventricular pulse generator 35. The control unit 24 generates trigger signals to the pulse generators to control both the rate and the inhibition of the stimulation pulses. Furthermore, the control unit 24 controls the rate at which the pulse generators generate stimulation pulses, as well as keeping track of the timing of any refractory period, PVARP intervals, noise detection windows, alert intervals, etc., as is known in the art.

The control unit 24 also controls an atrial detector 26, which includes amplifying/filtering circuitry, e.g. a pre-amplifier 28 followed by peak detector 34, as is well known in the art. Furthermore, the control unit 24 controls a ventricular detector 36, which includes amplifying/filtering circuitry, e.g. a pre-amplifier 38 followed by a peak detector 40, as is also well known in the art. Alternately, the function of blocks 34 and 40 may be combined into a single A/D converter that, when multiplexed, can measure the peak amplitude of the cardiac signals. Typically, the A/D converter is part of a separate system 42 for recording or transmitting intracardiac electrograms (IEGMs). In this embodiment, sequences of electrogram signals recorded by the sensing system 42 are continuously stored in the memory 30. Preferably, the length a sequence is about 500 ms, which is controlled by a timer 54 connected to the controlling unit 24. The atrial detector 26 and the ventricular detector 36 receive control signals over signal lines 44 and 46, respectively, for controlling the sensitivity (gain and thresholds) and the timing of any blanking circuitry (not shown) coupled to the inputs of the pre-amplifiers.

In this embodiment, an atrial signal is communicated to the peak detector 34 via the pre-amplifier 28. In certain embodiments, the peak detector may include a digital comparator and register, wherein the signal is continuously compared with an initial value stored in the peak detector 34, the current value is loaded into the register value and is then stored in the register. The peak detector 34 includes a clearing mechanism controlled by the control unit 24. The timer 54 activates and deactivates the peak detector 34. Alternatively, timers to activate and deactivate the peak detector 34 may also be included in the peak detector 34 itself. Once the peak detector 34 times out, the register value is communicated to the control unit 24. Thereafter, the value is communicated to threshold determining unit 47 coupled to the control unit 24, wherein the communicated value is processed in order to obtain sensing threshold. According to a preferred embodiment, the maximum value or peak value of the amplitudes of the atrial events, i.e. P-waves detected during a predetermined period of time, for example, 5 seconds, is multiplied in the threshold determining unit 47 with a pre-set coefficient, which preferably is a factor in the range of 0.2 and 0.95, and more preferably in the range of 0.4 and 0.9, for example, a factor of 0.75 in order to define a P-wave threshold value. Then, the control unit 24 can retrieve the first P-wave threshold value in the threshold determining unit 47 and thereby define a first sensing threshold, which is communicated to the atrial detector 26 in order to set the sensitivity settings.

An identifying/analyzing unit 52 is coupled to the control unit 24 and a sequence of IEGM signals retrieved from the memory 30 in order to detect atrial events in the sequence and determine amplitude peaks, which may be for example, P-waves or PACs.

FIG. 1 shows only one hardware configuration in which the present invention can be implemented. Those skilled in the art can appreciate that the circuit of FIG. 1 can be modified so that, for example, the threshold determining unit 47 can be internal to the control unit 24.

The operation of the automatic adjustment according to the present invention is based upon analysis of a sequence or a number of sequences of IEGM signals during a period preceding a detected ventricular depolarization event without a detected preceding atrial event. This may be due to that the detected R-wave was a part of a true PVC, or that the atrial sensing threshold was set too high to detect intrinsic atrial contractions as either P-waves or PACs. As used herein, the term "depolarization" refers to a detected intrinsic depolarization and not to a depolarization produced by a pacing pulse. Although pacing pulses produce cardiac depolarizations, these depolarizations are not usually detected by cardiac rhythm devices because the pre-amplifiers of the detecting means are "blanked" and the detecting channel rendered refractory for a predetermined period following a pacing pulse.

Figure 2:
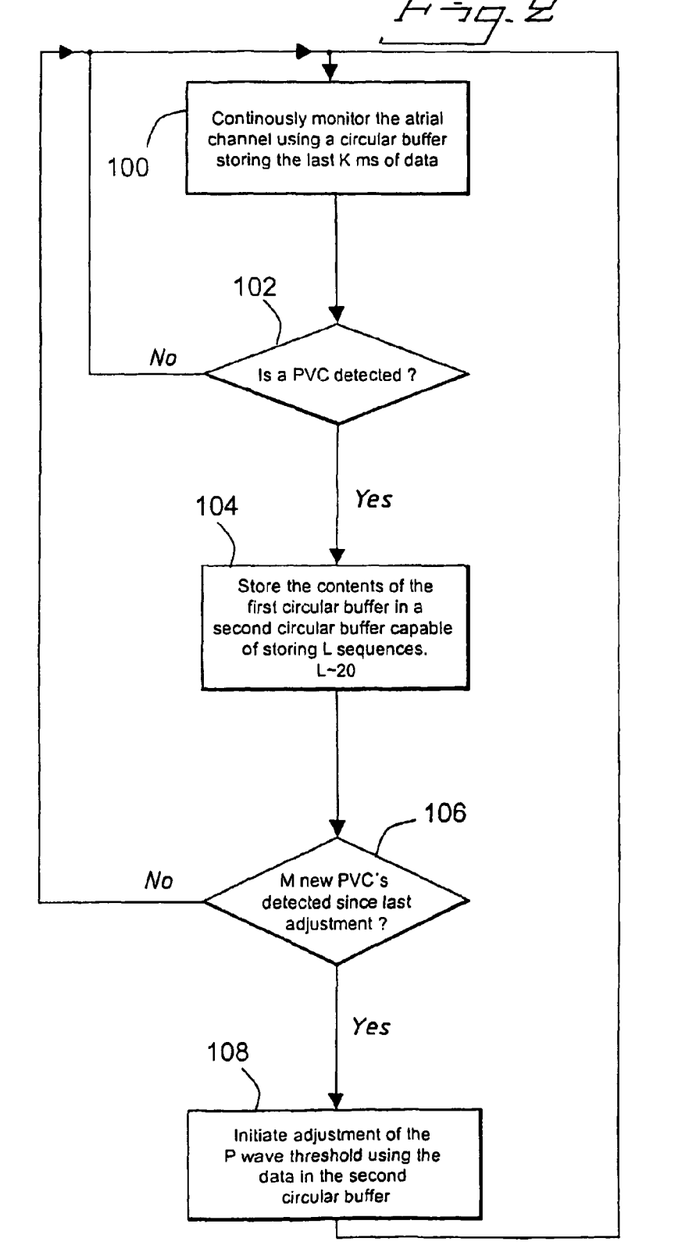
FIG. 2 is a flowchart of steps to implement one embodiment of the present invention.

With reference now to FIG. 2, the data collection performed during the normal operation of the device. In block 100, the atrial channel is continuously monitored in order to be able to store the data preceding a predetermined cardiac event, for example, a PVC. In this embodiment the last K ms of data are stored. Preferably, K is in the order of 500. The recorded data are stored in a circular buffer which, in this embodiment, is arranged in the memory 30.

In block 102 it is checked whether the predetermined event is detected, e.g. an R-wave without a preceding atrial event, or in other words, if a PVC (which in turn may be a "true" or a "false" PVC). If the predetermined event is detected, the K ms immediately preceding the ventricular event are retrieved from the first circular buffer and stored in a second circular buffer in block 104. The second circular buffer is also, in this embodiment, arranged in the storing means 30. Preferably, L is in the order of 20.

If, in block 106, M PVCs have been detected since the last adjustment of the P wave threshold, an adjustment mode is initiated at block 108. The adjustment mode will be described in more detail with reference to FIG. 3 below.

After the sequence or sequences have been analyzed and the sensing threshold adjusted to a level better adapted to the current situation of the patient, the stimulation device 10 returns to normal operation.

Figure 3:
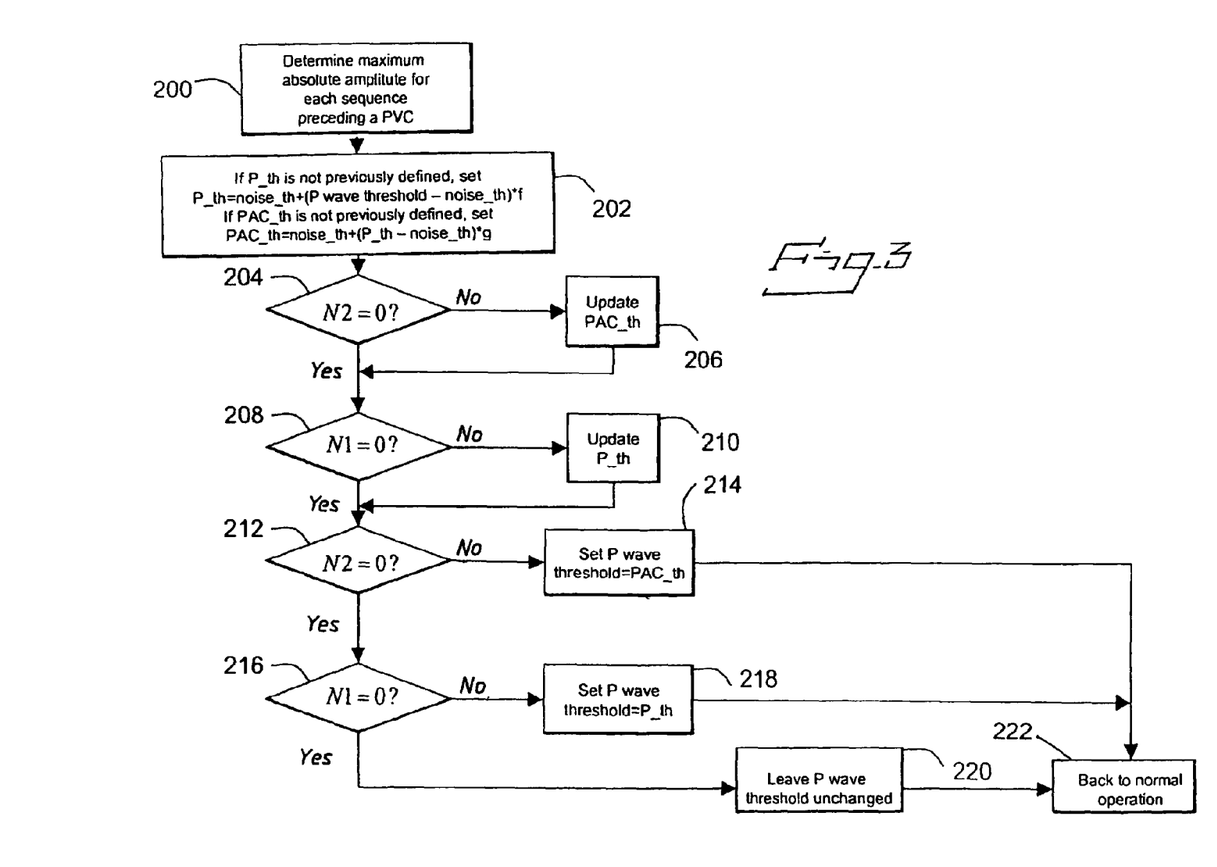
FIG. 3 is a flowchart of the further steps to be implemented in the embodiment of the present invention shown in FIG. 2.

With reference now to FIG. 3, the adjustment mode will be described in more detail. As mentioned above, the sequence or sequences of atrial IEGM signals stored in the second circular buffer is retrieved from the second circular buffer by the control unit 24, as described above, and communicated to the identifying/analyzing unit 52 for further analysis. Accordingly, the number of sequences may be larger than the number of PVCs initiating the adjustment procedure.

At block 200, a scanning of each of the retrieved sequences are performed and the maximum amplitude of the atrial events for each sequence are determined. Thereafter, if the automatic threshold adjustment function is run for the first time, two thresholds, P_th and PAC_th, are defined in block 202. P_th is defined according to the following:

$$P\_th = \text{noise\_th} + (P \text{ wave threshold} - \text{noise\_th}) * f. \tag{1}$$

PAC_th is defined according to the following:

$$PAC\_th = \text{noise\_th} + (P\_th - \text{noise\_th}) * g. \tag{2}$$

Where f is a pre-selected factor having a value between zero and one ($0 \leq f \leq 1$), and g a pre-selected factor having a value between zero and one ($0 \leq g \leq 1$). The P wave threshold is the actual P wave threshold of the sensitivity settings of the atrial detecting means 26 and noise_th is the noise threshold of the sensitivity settings. If the function has been run previously, these thresholds have already been defined.

Any deflections exceeding P_th are assumed to be low amplitude P waves (or high amplitude PAC's) and any deflections exceeding PAC_th, but not P-the are assumed to be PAC's.

At block 204, it is checked whether N2 is equal to zero, where N2 is a number set equal to the number of values between the PAC_th and the P_th. If no, at block 206, the PAC_th is updated according to the following procedure.

The new PAC_th is set according to:

$$PAC\_th\_\text{new} = PAC\_th\_\text{old} * (1 - k1) + k1 * x \tag{3}$$

where PAC_th_new is the updated PAC_th and PAC_th old is the preceding PAC_th, k1 is a coefficient between zero and one ($0 \leq k1 \leq 1$) and x can be any of the following:

1. the minimum amplitude of the events.
2. the median amplitude of the events.

3. the average amplitude of the events.
4. any function of the events.

If the answer to N1=0? is yes, the function proceeds to block 208, where it is checked whether N1 is equal to zero or no, where N1 is a number set equal to the number of values between the P_th and the P wave threshold. If no, at block 210, the P_th is updated according to the following procedure.

The new P_th is set according to:

$$P\_th\_\text{new} = P\_th\_\text{old} * (1-k2) + k2*y, \quad (3)$$

where P_th new is the updated P_th and P_th old is the preceding P_th, k2 is a coefficient between zero and one ($0 \leq k2 \leq 1$) and y can be any of the following:
1. the minimum amplitude of the events.
2. the median amplitude of the events.
3. the average amplitude of the events.
4. any function of the events.

If the answer to N1=0? is yes, the function proceeds to block 212, and if any PAC's have been found in the data sequences (i.e. if N2=0, no PACs were found), the P wave threshold is set to the updated PAC_th at block 214. Subsequently, at block 222, the controlling unit 24 terminates the adjustment mode, normal operation of the stimulation device 10 continues or is resumed with the new and adjusted P-wave threshold and the obtaining and storing of atrial IEGM sequences is continued.

On the other hand, if no PAC's have been found in the data sequences, the function proceeds to block 216 and if any low level P waves have been found (i.e. if N=0, no P waves were found), the P wave threshold is set to the updated P_th at block 218. Subsequently, at block 222, the controlling unit 24 terminates the adjustment mode, normal operation of the stimulation device 10 continues or is resumed with the new and adjusted P-wave threshold and the obtaining and storing of atrial IEGM sequences is continued.

On the other hand, if no low level P waves have been found, i.e. N1 is equal to zero, the function proceeds to block 220 and the P wave threshold is left unchanged. Subsequently, at block 222, the control unit 24 terminates the adjustment mode, normal operation of the stimulation device 10 continues or is resumed with the new and adjusted P-wave threshold and the obtaining and storing of atrial IEGM sequences is continued.

Utilizing the above described automatic adjustment function, the sensitivity of the atrial detector 26 can be greatly improved and, consequently, it is possible to detect PAC's having significantly lower amplitudes than sinus induced P-waves. Accordingly, it is possible to distinguish between true and false PVCs.

Figure 4:
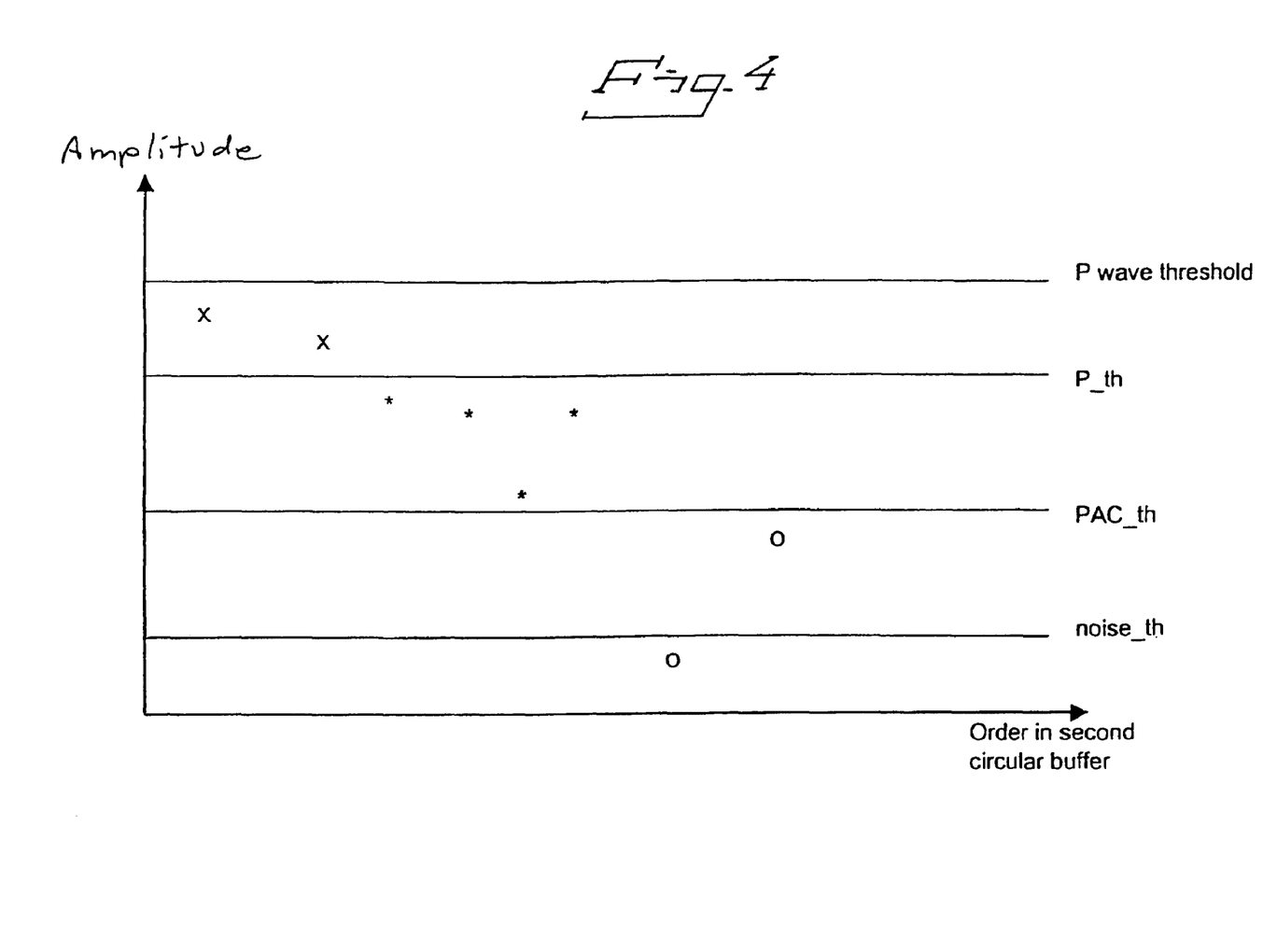
FIG. 4 is schematic graph of the P-wave threshold, the PAC threshold, and the minimum threshold during an adjustment mode.

With reference now to FIG. 4, a typical distribution of the amplitudes in the sequences stored in the second circular is shown. At the initiation of the adjustment mode, for example at the detection of M PVCs, only a P-wave threshold and a minimum or noise threshold are defined. These thresholds are also used by the atrial detecting means at the detection of P-waves during the normal operation of the stimulation device 10, for example in the DDD mode. As described above, the control unit 24 retrieves the sequence or the sequences of atrial IEGM signals that preceded the detected PVC(s) from the circular buffer of the memory 30, scans or analyses the sequence(-s) by means of the identifying/analyzing means 52 in order to identify atrial events. The amplitude of each identified event is measured. It should be noted that since each sequence is short, for example, 500 ms, only a few number of events are likely to occur during the duration of a sequence.

If the automatic threshold adjustment function is run for the first time two thresholds, P_th and PAC_th, are defined according to equations (1) and (2). If the function has been run previously, these thresholds have already been defined.

According to the preferred embodiment, an atria/event is defined as a P-wave and the current P-wave threshold is maintained if a measured amplitude of a identified event is found to be above the current P-wave threshold. If an measured amplitude of a identified event is found to be within the interval formed between the P wave threshold and the P_th level, the event is defined as a low level P wave, indicated with the symbol "x" in FIG. 4. If a measured amplitude of a identified event is found to be within the interval formed between the P_th level and the PAC_th level, the event is defined as a PAC, indicated with the symbol "*" in FIG. 4. In this case, N1 will be equal to 2 and N2 will be equal to 4 and, accordingly, L is equal to 8. Furthermore, if the measured amplitude of an identified event is found to be below the PAC_th level, the event is disregarded as an event originating from a true PVC, indicated with the symbol "o" in FIG. 4.

When the sequence or sequences has been scanned for atrial events and adjustments, if any, in accordance with the above-mentioned procedure have been conducted, the control unit 24 interrupts the adjustment mode and returns to normal operation, see FIG. 3. Thereby, the sensitivity of the detector 26 is greatly improved and it is possible to detect also PACs having a significantly smaller amplitudes than P-waves.

In the embodiment described above, in particular with reference to FIG. 2, an adjustment mode was initiated when M PVCs were detected. However, there are a number of other conceivable events, series of events, or states that may be used to initiate an adjustment mode. As an example, an atrial stimulation can be used to initiate the adjustment mode and, accordingly, initiate the controlling unit to retrieve a sequence or a number of sequences of IEGM signals in order to adjust the current sensing threshold of the sensitivity settings by analyzing the sequence(s) according to above described procedure. The fact that an atrial stimulation occurs may, for example, be due to that the sensitivity settings of the atrial detecting means is set too high, which, in turn, entails that P-waves having a low amplitude are not detected. In this case, the sequences immediately preceding the R-wave caused by the atrial stimulation should be used in the analysis. According to another example, both an atrial stimulation and a ventricular stimulation can be used as the cardiac event initiating the adjustment mode.

In accordance with another embodiment, a long sequence, for example, 25 seconds, can be stored and used to obtain information regarding the relation between PACs and P-waves using the procedure described with reference to FIG. 3. This information can be very useful for diagnostic purposes.

Although an exemplary embodiment of the present invention has been shown and described, it will be apparent to those having ordinary skill in the art that a number of changes, modifications, or alterations to the invention as described herein may be made. Thus, it is to be understood that the above description of the invention and the accompanying drawings is to be regarded as a non-limiting example thereof and that the scope of protection is defined by the appended patent claims.

We claim as our invention:
1. An implantable cardiac stimulation device comprising:
an atrial detector having an amplifier configured to detect incoming atrial IEGM signals that may include a P-wave, said atrial detector having adjustable sensitivity settings to detect said incoming IEGM atrial signals;

a control unit connected to said atrial detector supplied with the atrial IEGM signals detected by said atrial detector, said control unit being configured to set the sensitivity of the atrial detector to a current one of said sensitivity settings corresponding to an expected P-wave amplitude in order to give the atrial detector a sensitivity that causes said atrial detector to detect a P-wave, if present in said IEGM signals, that has an amplitude above said expected P-wave amplitude;

a ventricular detector that detects ventricular contractions;

said control unit being connected to said ventricular detector and being configured to generate a signal indicating an occurrence of a premature ventricular contraction (PVC) when a ventricular contraction is detected by said ventricular detector that was not immediately preceded by detection of a P-wave in the IEGM signals detected by said atrial detector;

a memory;

a sensing unit, separate from said atrial detector and from said ventricular detector, also configured to receive said incoming atrial IEGM signals, said sensing unit being configured to, within a limited time duration, enter actual signal portions of said IEGM signals that occur in said limited time duration into said memory independently of whether said signal portions are detected by said atrial detector, said signal portions of said IEGM signals in said memory each having a predetermined signal portion length;

an analyzing unit, having access to the memory, configured to execute an analysis routine to identify whether a signal portion detected by said sensing unit and stored in said memory contains a P-wave having a lower amplitude than said current sensitivity setting;

a threshold determining unit connected to said analyzing unit, said threshold determining unit, if said analyzing unit identifies P-waves, detected by said sensing unit and stored in said memory, having a lower amplitude than said current sensitivity setting, setting a threshold for a new sensitivity setting for said atrial detector based on said P-waves detected by said sensing unit and stored in said memory and identified in said signal portion by said analyzing unit; and said control unit being connected to said threshold determining unit and changing said current sensitivity setting to said new sensitivity setting, having said threshold determined by said threshold determining unit, to cause said atrial detector to detect all atrial events so as to configure said control unit to avoid false PVC indications due to a P-wave being present in said IEGM signals but undetected by said atrial detector.

2. An implantable cardiac stimulation device as claimed in claim 1 wherein said control unit, upon detection of a predetermined cardiac event in said atrial signals that pass through said atrial detector, causes said analyzing unit to execute said analysis routing for a sequence of said IEGM signals in said memory that immediately precedes said predetermined cardiac event.

3. An implantable cardiac stimulation device as claimed in claim 1 wherein said control unit automatically determines a highest allowable sensitivity setting for said atrial detector by analyzing an actual noise level of said atrial detector.

4. An implantable cardiac stimulation device as claimed in claim 1 wherein said control unit sets said atrial detector to an initial sensitivity setting determined by a measured amplitude of a P-wave detected by said atrial detector, multiplied by a factor in a range between 0.4 and 0.9.

* * * * *